United States Patent [19]

Gutman

[11] 4,425,271
[45] Jan. 10, 1984

[54] 2,6-DICHLOROPHENYL-SUBSTITUTED PHENYL-NITROA-ZONES AND THEIR USE AS HERBICIDES

[75] Inventor: Arnold D. Gutman, Berkeley, Calif.

[73] Assignee: Stauffer Chemical Company, Westport, Conn.

[21] Appl. No.: 219,278

[22] Filed: Dec. 22, 1980

Related U.S. Application Data

[62] Division of Ser. No. 54,323, Jul. 2, 1979, Pat. No. 4,270,947.

[51] Int. Cl.³ .................. C07C 107/04; A01N 9/12; A01N 9/20
[52] U.S. Cl. ....................... 260/192; 71/121; 71/98; 260/193
[58] Field of Search ................. 260/192, 193

[56] References Cited

U.S. PATENT DOCUMENTS 3,830,642  8/1974  Moon .................. 260/192 X
3,834,892  9/1974  Moon et al. .......... 260/192 X

OTHER PUBLICATIONS

Hunter et al., Chemical Abstracts, vol. 36, 1915, 4–9, (1942).

*Primary Examiner*—Floyd D. Higel
*Attorney, Agent, or Firm*—Edwin H. Baker

[57] ABSTRACT

Compounds having the structural formula

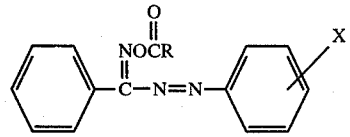

wherein R is alkyl, cycloalkyl, haloalkyl, alkenyl, alkylthio, alkoxy, —NH-alkyl,

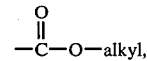

phenyl or monohalophenyl; and X is hydrogen; alkyl; monohalo; dihalo or nitro and intermediate compounds having the structural formula

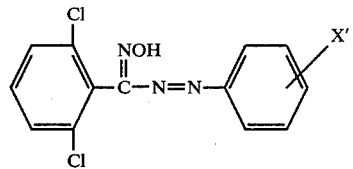

wherein X' is defined as above excluding hydrogen, both of which compounds are useful as herbicides.

2 Claims, No Drawings

2,6-DICHLOROPHENYL-SUBSTITUTED PHENYL-NITROA-ZONES AND THEIR USE AS HERBICIDES

This is a division of application Ser. No. 054,323, filed July 2, 1979, now U.S. Pat. No. 4,272,947.

DESCRIPTION OF THE INVENTION

This invention relates to certain novel α-(phenylazo)-2,6-dichlorobenzaldimino esters and their use as herbicides. These compounds have the following structural formula

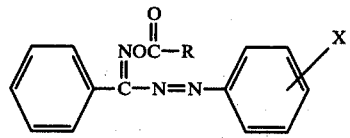

wherein R is alkyl having 1 to 4 carbon atoms, preferably methyl; cycloalkyl having 3 to 6 carbon atoms, preferably cyclopropyl; haloalkyl having 1 to 4 carbon atoms, preferably bromomethyl; dichloromethyl or trichloromethyl; alkenyl having 2 to 4 carbon atoms, preferably 1-methyl vinyl; alkylthio having 1 to 4 carbon atoms, preferably methylthio and ethylthio; alkoxy having 1 to 4 carbon atoms, preferably ethoxy; —NH-alkyl having 1 to 4 carbon atoms, preferably —NHCH$_3$;

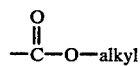

having 1 to 4 carbon atoms, preferably

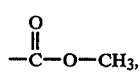

phenyl and monohalophenyl, preferably chlorophenyl; X is hydrogen, alkyl having 1 to 4 carbon atoms, preferably methyl, monohalo, preferably chloro; dihalo, preferably dichloro or nitro.

In the above description of the compounds of the invention, the term alkyl includes both straight chain and branch chain configurations. For example, alkyl can be methyl, ethyl, n-propyl, n-butyl, sec-butyl or tert-butyl.

The term haloalkyl includes mono, di and tri chloro, bromo or fluoro alkyl. Also, the prefix halo includes chloro, bromo and fluoro.

Another embodiment of this invention relates to certain novel 2,6-dichlorophenyl-phenylnitrosazone intermediate compounds which are useful as herbicides. These intermediate compounds have the following structural formula

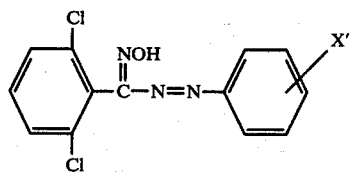

wherein X' is defined as above, excluding hydrogen.

The compounds of this invention can be prepared according to the following reaction steps:

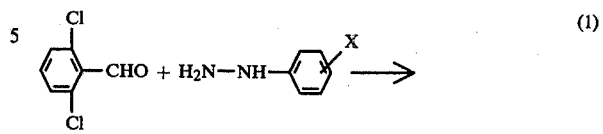

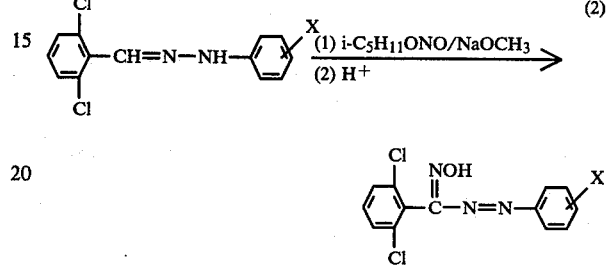

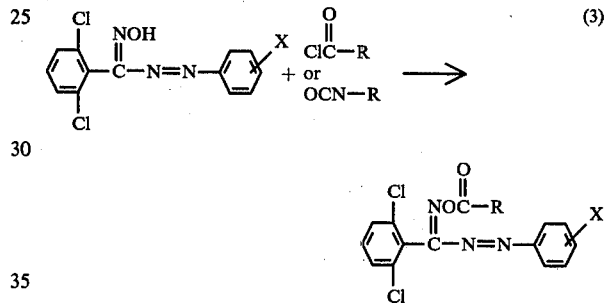

wherein X and R are as defined.

Preferably reaction step 1 is carried out by combining an equimole amount of 2,6-dichlorobenzaldehyde to a solution of the appropriate phenylhydrazine in a solvent such as alcohol, toluene, or methylenechloride, preferably ethanol, with stirring at a temperature range of 20°–40° C. The reaction is continued for 2–4 hours with stirring. After the reaction is complete, the 2,6-dichlorobenzaldehyde phenylhydrazone product is recovered by filtration.

Preferably, reaction step 2 is carried out by adding an equimole amount of the hydrazone reaction product of reaction step 1 to a reaction vessel containing a solution of a strong base such as a 25 percent solution of sodium methoxide in a solvent such as methanol. The resulting solution is stirred with the addition of about two mole of a higher alkyl nitrite such as amylnitrite, isoamylnitrite or butylnitrite. The reaction mixture is refluxed for about one hour, cooled and the solvent removed by vacuum stripping. The residue is titurated with ether, dissolved in water and acidified with dilute hydrochloric acid to yield the desired oxime which is cooled by filtration, washed with water and dried.

The oxime from reaction step 2 is useful as a herbicide or it can be further reacted with an appropriate acid chloride, chloroformate, chlorothioformate or isocyanate. The resulting reaction product is also useful as a herbicide.

Preferably reaction step 3 is carried out in the presence of an equimole amount of acceptor such as dimethylaniline, pyridine, sodium hydroxide or preferably triethylamine in a suitable solvent such as acetone, toluene, ether, tetrahydrofuran or alcohol, preferably methylenechloride by slowly adding an equimole amount of an appropriate acid chloride, chloroformate or chlorothioformate to a stirred solution of the oxime reaction product of reaction step 2 at a temperature range of 0°–10° C. The reaction is allowed to warm to room temperature and is stirred for about one hour. The desired reaction product is recovered and purified by conventional means to yield the desired product. When the oxime reaction product of reaction step 2 is reacted with a suitable isocyanate, the procedure is as defined above except that a solvent such as acetone, toluene, tetrahydrofuran or preferably methylene chloride is used to yield the desired product.

The following Examples 1–3 teach the synthesis of representative intermediate compounds of this invention according to reaction step 2.

EXAMPLE I 2,6-Dichlorophenyl-phenylnitrosazone

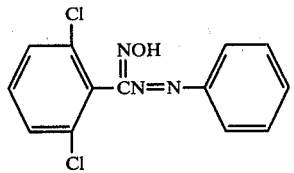

First, 55.8 grams (g) (0.21 mole) 2,6-dichlorobenzaldehyde phenylhydrazone was charged to a 3-neck round bottom flask, equipped with a stirrer, thermometer, condenser and containing a previously added solution of 25 percent sodium methoxide (45.4 g—0.21 mole) in 150 milliliters (ml) methanol. To the stirring solution was added isoamylnitrite (49.1 g—0.42 mole). The reaction was refluxed for one hour and after cooling the methanol was removed under vacuum. The residue was dissolved in ether, washed with water and the water layer acidified with diluted HCl. The resulting solid was collected and dried. Yield: 13.3 g, m.p. 145°–147° C. Structure was confirmed by nuclear magnetic resonance (NMR).

EXAMPLE 2

2,6-Dichlorophenyl-3-tolylnitroazone

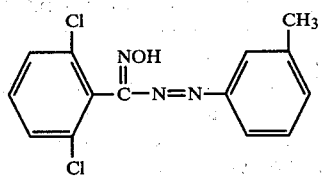

In the same manner as Example 1, 16.4 g (0.06 mole) 2,6-dichlorobenzaldehyde-3-tolylhydrazone, 14.0 g (0.012 mole) isoamylnitrite, 13.0 g (0.06 mole) and 25% sodium methoxide were combined in 150 ml of methanol to yield 5.9 g of the desired product. m.p. 156°–158° C. The structure was confirmed by NMR.

EXAMPLE 3

2,6-Dichlorophenyl-4-nitrophenyl-nitroazone

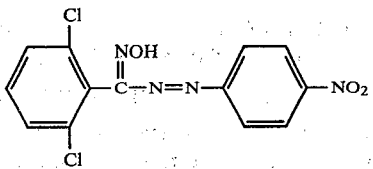

In the same manner as Example 1, 40.0 g (0.13 mole) 2,6-dichlorobenzaldehyde-4-nitrophenylhydrazone, 30.4 g (0.26 mole) isoamylnitrite and 28.0 g (0.13 mole) 25% sodium methoxide were combined in 300 ml of methanol to yield 20.4 g of the desired product. m.p. 157°–159° C. The structure was confirmed by NMR.

The following Examples 4–8 teach the synthesis of representative compounds of this invention according to reaction step 3.

EXAMPLE 4

α-(Phenylazo)-2,6-dichlorobenzaldiminochloroacetate

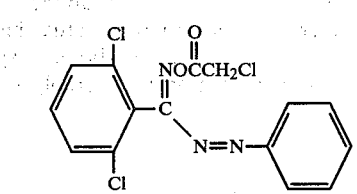

3.0 g (0.01 mole) of the product from Example 1 was dissolved in 100 ml methylenechloride using a 1-neck 250 ml round bottom flask with a magnetic stirrer. 1.0 g (0.01 mole) triethylamine was added and the mixture was cooled to 0° C. To the stirring solution, 1.1 g (0.01 mole) chloroacetylchloride was slowly added over a period of 10 minutes. The reaction was allowed to warm to room temperature and was stirred for one hour. The reaction mass was then washed with 2-100 ml portions of water, dried with anhydrous MgSO4, filtered and evaporated in vacuo to yield: 3.4 g of the desired product. The structure was confirmed by mass spectroscopy.

EXAMPLE 5

α-(Phenylazo)-2,6-dichlorobenzaldiminomethacrylate

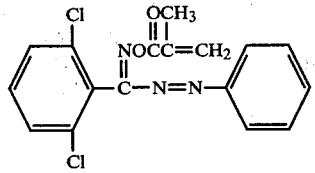

In the same manner as in Example 4, 3.5 g (0.012 mole) of product from Example 1, 1.3 g (0.02 mole) methacrylchloride and 1.2 g (0.012 mole) of triethylamine were combined in 100 ml of methylene chloride to yield 3.5 g of the desired product (semi-solid). The structure was confirmed by NMR.

EXAMPLE 6

α-Phenylazo-2,6-dichlorobenzaldimino-2-chloropropionate

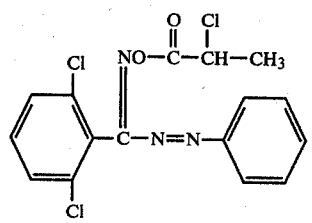

In the same manner as in Example 4, 3.5 g (0.012 mole) product from Example 1, 1.5 g (0.012 mole) 2-chloropropionylchloride and 1.2 g (0.012 mole) of methylamine were combined in 100 ml of methylenechloride to yield 4.9 g of the desired product (semi-solid). The structure was confirmed by NMR.

EXAMPLE 7

α-Phenylazo-2,6-dichlorobenzaldiminobromoacetate

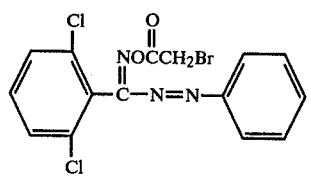

In the same manner as Example 4, 3.5 g (0.012 mole) product from Example 1, 2.4 g (0.012 mole) bromoacetylbromide and 1.2 g (0.012 mole) of triethylamine were combined in 100 ml of methylenechloride to yield 5.0 g of the desired product. $n_D^{30}$ 1.6100. The structure was confirmed by NMR.

EXAMPLE 8

α(3-Tolylazo)-2,6-dichlorobenzaldiminotrichloroacetate

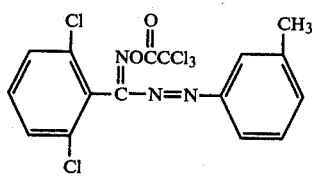

In the same manner as Example 4, 2.4 g (0.0086 mole) product from Example 2, 1.6 g (0.0086 mole) trichloroacetylchloride and 0.9 g (0.0086 mole) of triethylamine were combined in 100 ml of methylenechloride to yield 3.1 g of the desired product (semi-solid). The structure was confirmed by NMR.

The following are tables of certain selected compounds that were prepared according to the procedures described herein. Compound numbers are assigned to each compound and are used throughout the remainder of the specification.

TABLE 1

| Compound Number | X | M.P. °C. |
|---|---|---|
| 1 | 3-CH$_3$ | 156–158 |
| 2 | 3,4-Cl$_2$ | 186–188 |
| 3[b] | 4-NO$_2$ | 157–158 |
| 4 | 2-Cl | 153–156 |
| 5 | 4-Cl | 127–130 |
| 6 | 2,4-Cl$_2$ | 151–154 |
| 7 | 4-Br | 148–150 |
| 8 | 3-NO$_2$ | 104–106 |
| 9 | 2,6-Cl$_2$ | 110–115 |
| 10 | 2,5-Cl$_2$ | 173–175 |
| 11[a] | 2-CH$_3$ | 172–174 |
| 12 | 3-Cl | 176–177 |
| 13 | 2-Br | 142–146 |
| 14 | 3-Br | 174–177 |
| 15 | 4-CH$_3$ | 116–120 |
| 16 | 4-F | 98–100 |

[a]Prepared in Example 2
[b]Prepared in Example 3

TABLE 2

| Compound Number | R | X | $n_D^{30}$ or M.P. °C. |
|---|---|---|---|
| 17[c] | —CH$_2$Cl | H | semi-solid |
| 18 | —CHCl$_2$ | H | 1.5930 |
| 19 | —CH$_2$Cl | 3-CH$_3$ | semi-solid |
| 20[g] | —CCl$_3$ | 3-CH$_3$ | semi-solid |
| 21 | —NHCH$_3$ | 3,4-Cl$_2$ | 184–186 |
| 22 | —CH$_2$Cl | 3,4-Cl$_2$ | 87–90 |
| 23 | cyclopropyl | 3,4-Cl$_2$ | 110–112 |
| 24[d] | —C(CH$_3$)=CH$_2$ | H | semi-solid |
| 25[e] | —CHClCH$_3$ | H | semi-solid |
| 26[f] | —CH=CH$_2$ | H | semi-solid |
| 27 | —CH$_2$Br | H | semi-solid |
| 28 | —CH$_2$CH$_2$Br | H | semi-solid |
| 29 | —CHBrCH$_3$ | H | low melting material |
| 30 | —COC$_2$H$_5$ | H | 1.5962 |
| 31 | —C(CH$_3$)$_3$ | H | 65–68 |
| 32 | —CH$_3$ | H | 1.5860 |

TABLE 2-continued structure: benzene ring with NOC(=O)-R group above, C=N-N= linked to phenyl-X ring

| Compound Number | R | X | $n_D^{30}$ or M.P. °C. |
|---|---|---|---|
| 33 | $-\underset{\underset{CH_2}{\parallel}}{\overset{CH_3}{C}}$ | H | 99–105° |
| 34 | $-\underset{\underset{CH_3}{\mid}}{\overset{Cl}{CH}}$ | 4-NO$_2$ | 1.5900 |
| 35 | —CH=CH$_2$ | 4-NO$_2$ | 130–133 |
| 36 | —CH$_2$Br | 4-NO$_2$ | semi-solid |
| 37 | —CH$_2$CH$_2$Br | 4-NO$_2$ | semi-solid |
| 38 | $-\underset{\underset{CH_3}{\mid}}{\overset{Br}{CH}}$ | 4-NO$_2$ | semi-solid |
| 39 | $-\underset{\underset{CH_3}{\mid}}{\overset{CH_3}{\underset{\mid}{C}}}-CH_3$ | 4-NO$_2$ | semi-solid |
| 40 | —CH=CH$_2$ | 3,4-Cl$_2$ | low melting material |
| 41 | —CH$_2$CH$_2$Br | 3,4-Cl$_2$ | low melting material |
| 42 | $-\underset{\underset{CH_3}{\mid}}{\overset{Br}{CH}}$ | 3,4-Cl$_2$ | low melting material |
| 43 | $-\underset{\underset{CH_3}{\mid}}{\overset{CH_3}{C}}-CH_3$ | 3,4-Cl$_2$ | semi-solid |
| 44 | —OC$_2$H$_5$ | H | 122–125 |
| 45 | —OCH$_2$CH$_2$Cl | H | semi-solid |
| 46 | —C$_6$H$_5$ (phenyl) | H | 124–129 |
| 47 | —C$_6$H$_4$-Cl | H | 138–141 |
| 48 | —SC$_2$H$_5$ | H | 72–74 |
| 49 | $-\underset{\underset{CH_3}{\mid}}{\overset{Cl}{CH}}$ | 2-Cl | 1.6120 |
| 50 | $-\underset{\underset{CH_3}{\mid}}{\overset{Br}{CH}}$ | 2-Cl | 1.6222 |
| 51 | —CH$_3$ | 2-Cl | 1.6240 |
| 52 | —CH=CH$_2$ | 2-Cl | semi-solid |
| 53 | —C$_6$H$_5$ (phenyl) | 2-Cl | 122–127 |
| 54 | —CH$_2$Cl | 4-Cl | 1.6252 |
| 55 | $-\underset{\underset{CH_3}{\mid}}{\overset{Cl}{CH}}$ | 4-Cl | 1.6416 |
| 56 | —CH$_2$CH$_2$Br | 4-Cl | 95–99 |
| 57 | $-\underset{\underset{CH_3}{\mid}}{\overset{Br}{CH}}$ | 4-Cl | semi-solid |
| 58 | —OC$_2$H$_5$ | 4-Cl | 97–99 |
| 59 | —C$_6$H$_4$-Cl | 4-Cl | 168–171 |
| 60 | —SC$_2$H$_5$ | 4-Cl | 59–62 |
| 61 | —CH$_2$Cl | 2,4-Cl$_2$ | semi-solid |
| 62 | $-\underset{\underset{CH_2}{\parallel}}{\overset{CH_3}{C}}$ | 2,4-Cl$_2$ | 86–90 |
| 63 | $-\underset{\underset{CH_3}{\mid}}{\overset{Cl}{CH}}$ | 2,4-Cl$_2$ | semi-solid |
| 64 | $-\underset{\underset{CH_3}{\mid}}{\overset{Br}{CH}}$ | 2,4-Cl$_2$ | semi-solid |
| 65 | —OC$_2$H$_5$ | 2,4-Cl$_2$ | low melting material |
| 66 | —C$_6$H$_5$ (phenyl) | 2,4-Cl$_2$ | 114–116 |
| 67 | —OC$_2$H$_5$ | 4-NO$_2$ | 35–36 |
| 68 | —CH$_2$Cl | 4-Br | semi-solid |
| 69 | —CH$_2$Cl | 3-NO$_2$ | 126–128 |
| 70 | —CH$_2$Cl | 2,6-Cl$_2$ | semi-solid |
| 71 | —CH$_2$Cl | 2-CH$_3$ | 85–89 |
| 72 | —CH$_2$Cl | 3-Cl | semi-solid |
| 73 | —CH$_2$Cl | 2-Br | semi-solid |
| 74 | —CH$_2$Cl | 4-F | semi-solid |
| 75 | —SCH$_3$ | 2-CH$_3$ | 64–67 |
| 76 | —SC$_2$H$_5$ | 2-CH$_3$ | 63–66 |
| 77 | —SCH$_3$ | 4-CH$_3$ | 121–125 |
| 78 | —SC$_3$H$_7$-n | 3-Cl | 48–56 |
| 79 | —SC$_2$H$_5$ | 3-Cl | 80–83 |
| 80 | —SC$_2$H$_5$ | 3-NO$_2$ | 73–76 |
| 81 | —SC$_3$H$_7$-i | 3-NO$_2$ | semi-solid |
| 82 | —SC$_4$H$_9$-n | 3-Br | semi-solid |

$^c$Prepared in Example 4
$^d$Prepared in Example 5
$^e$Prepared in Example 6
$^f$Prepared in Example 7
$^g$Prepared in Example 8

Herbicidal Screening Tests

As previously mentioned, the herein described compounds produced in the above-described manner are phytotoxic compounds which are useful and valuable in controlling various plant species. Selected compounds of this invention are tested as herbicides in the following manner.

Pre-emergence herbicide test. On the day preceding treatment, seeds of seven different weed species are planted in loamy sand soil in individual rows using one species per row across the width of a flat. The seeds used are hairy crabgrass (*Digitaris sanguinalis*), green foxtail *Setaria viridis*), watergrass (*Echinochloa crusgalli*), California red oat (*Avena sativa*), redroot pigweed (*Amaranthus retroflexus*), Indian mustard (*Brassica juncea*) and curly dock (*Rumex crispus*). Ample seeds are planted to give about 20 to 50 seedlings per row, after emergence, depending upon the size of the plants. The flats are watered after planting.

Using an analytical balance, 20 milligrams (mg) of the compound to be tested was weighed out on a piece of glassine weighing paper. The paper and compound were placed in a 30 ml wide-mouth bottle and 3 ml of acetone containing 1% polyoxyethylene sorbitan monolaurate emulsifier was added to dissolve the compound. If the material was not soluble in acetone, another solvent such as water, alcohol or dimethylformamide (DMF) was used instead. When DMF was used, only 0.5 ml or less was used to make the volume up to 3 ml. The 3 ml solution was sprayed uniformly on the soil contained in a flat one day after planting weed seeds in the flat of soil. A No. 152 DeVilbiss atomizer was used to apply the spray using a compressed air at a pressure of 5 lb/sq. inch (0.35 Kg/Cm$^2$). The rate of application was 8 lb/acre (8.97 Kg/ha) and the spray volume was 143 gallon/acre (1338 L/n).

When a lower application rate is desired, the above-described pre-emergence herbicide test is used except that the seeds of California red oat are replaced with wild oat (*Avena fatua*) and tubers of yellow nutsedge (*Cyprus esculentus*) are additionally planted in the flat. Also, 300 mg of the compound to be tested is placed in a 2 oz. amber bottle and dissolved in 45 ml of acetone or substitute solvent as described above. Twenty ml of this solution are transferred to a 80 ml wide-mouth amber bottle and diluted with 24.5 ml of a water and acetone mixture (10:1) containing 1% polyoxyethylene sorbitan monolaurate emulsifier. The solution is then sprayed on a seeded flat on a linear spray table calibrated to deliver 80 gallons per acre (748 L/ha). The application rate is 2 lb/acre (2.24 Kg/ha).

After treatment, the flats are placed in the greenhouse at a temperature of 70° to 85° F. and watered by sprinkling. Two weeks after treatment, the degree of injury or control is determined by comparison with untreated check plants of the same age. The injury rating from 0 to 100% are recorded for each species as percent control with 0% representing no injury and 100% representing complete control.

The results of these tests are shown in the following Table 3.

TABLE 3

| Compound Number | Percent Control |
|---|---|
| Pre-Emergence Herbicide Test Application Rate - 8 lbs. Per Acre | |
| 1 | 97 |
| 2 | 82 |
| 3 | 99 |
| 17 | 98 |
| 18 | 88 |
| 19 | 95 |
| 20 | 91 |
| 21 | 61 |
| 22 | 85 |
| 23 | 71 |
| 24 | 93 |
| 25 | 99 |
| 26 | 94 |
| 27 | 93 |
| 28 | 98 |
| 29 | 70 |
| 30 | 100 |
| 31 | 78 |
| 32 | 100 |
| 33 | 93 |
| 34 | 99 |
| 35 | 98 |
| 36 | 100 |
| 37 | 47 |
| 38 | 93 |
| 39 | 82 |
| 40 | 30 |
| 41 | 47 |
| 42 | 43 |
| 43 | 45 |
| 53 | 25 |
| 54 | 84 |
| 56 | 82 |
| 59 | 19 |
| 62 | 81 |
| 63 | 62 |
| 64 | 89 |
| 65 | 57 |
| Pre-Emergence Herbicide Test Application Rate - 2 lbs. Per Acre | |
| 4 | 40 |
| 5 | 32 |
| 6 | 24 |
| 7 | 15 |
| 8 | 29 |
| 9 | 37 |
| 10 | 39 |
| 11 | 16 |
| 12 | 25 |
| 13 | 29 |
| 14 | 35 |
| 15 | 38 |
| 16 | 20 |
| 44 | 48 |
| 45 | 42 |
| 46 | 27 |
| 47 | 17 |
| 48 | 40 |
| 49 | 25 |
| 50 | 39 |
| 51 | 18 |
| 52 | 25 |
| 55 | 24 |
| 57 | 34 |
| 58 | 39 |
| 60 | 58 |
| 61 | 24 |
| 66 | 10 |
| 67 | 14 |
| 68 | 25 |
| 69 | 10 |
| 70 | 35 |
| 71 | 23 |
| 72 | 29 |
| 73 | 28 |
| 74 | 32 |
| 75 | 67 |
| 76 | 15 |
| 77 | 33 |
| 78 | 33 |
| 79 | 29 |
| 80 | 29 |
| 81 | 13 |
| 82 | 65 |

The compounds of the present invention are useful as herbicides especially as pre-emergence herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to 10 pounds per acre.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of whic are available in commerce. The surface-active agent, when used, normally comprises from 0.1% to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to convention methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-s-triazine, 2-chloro-4-ethylamino-6-isopropylamino-s-triazine, and 2-ethylamino-4-isopropylamino-6-methyl-mercapto-s-triazine; urea derivatives, such as 3-(3,4-dichlorophenyl)-1,1-dimethyl urea and 3-(p-chlorophenyl)-1,1-dimethyl urea; and acetamides such as N,N-diallyl-α-chloroacetamide, and the like; benzoic acids such as 3-amino-2,5-dichlorobenzoic; thiocarbamates, such as S-propyl dipropylthiocarbamate, S-ethyl-dipropylthiocarbamate, S-ethyl cyclohexylethyl thiocarbamate, S-ethyl hexahydro-1H-azepine-1-carbothioate and the like; 4-(methylsulfonyl)-2,6-dinitro-N,N-substituted anilines, such as 4-(methylsulfonyl)-2,6-dinitro-N,N-substituted anilines, such as 4-trifluoromethyl-2,6-dinitro-N,N-di-n-propyl aniline and 4-trifluoromethyl-2,6-dinitro-N-ethyl-N-n-butyl aniline. Fertilizers useful in combination with the active ingredients include, for example, ammonium nitrate, urea and superphosphate. Other useful additaments include materials in which plant organisms take root and grow such as compost, manure, humus, sand and the like.

I claim:

1. A compound having the following structural formula

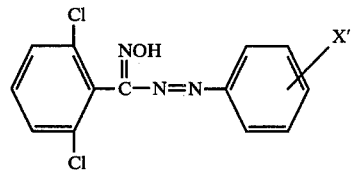

wherein X' is alkyl having 1 to 4 carbon atoms; monohalo; dihalo, or nitro.

2. The compound of claim 1 wherein X is 4-nitro.

UNITED STATES PATENT AND TRADEMARK OFFICE
CERTIFICATE OF CORRECTION

PATENT NO. : 4,425,271
DATED : January 10, 1984
INVENTOR(S) : Arnold D. Gutman

It is certified that error appears in the above-identified patent and that said Letters Patent are hereby corrected as shown below:

In Column 1, at line 7, the number "4,272,947" should read --- 4,270,947 ---.

Signed and Sealed this

Twenty-fourth Day of December 1985

[SEAL]

Attest:

DONALD J. QUIGG

Attesting Officer

Commissioner of Patents and Trademarks